United States Patent
Anazawa et al.

[11] Patent Number: 5,938,908
[45] Date of Patent: Aug. 17, 1999

[54] CAPILLARY ARRAY ELECTROPHORESIS SYSTEM

[75] Inventors: Takashi Anazawa, Kokubunji; Hideki Kambara, Hachioji; Satoshi Takahashi, Kunitachi; Kazumichi Imai, Hitachinaka; Hisanori Nasu, Yokohama, all of Japan

[73] Assignees: Hitachi, Ltd., Tokyo; Hitachi Software Engineering Co., Ltd., Yokohama, both of Japan

[21] Appl. No.: 08/847,735

[22] Filed: Apr. 22, 1997

[30] Foreign Application Priority Data

Apr. 23, 1996 [JP] Japan .................................. 8-100889

[51] Int. Cl.⁶ .................................................. G01N 27/26
[52] U.S. Cl. .......................................... 204/603; 356/344
[58] Field of Search .................................... 204/451, 603; 7/452, 601; 356/344

[56] References Cited

U.S. PATENT DOCUMENTS

| | | | |
|---|---|---|---|
| 5,529,679 | 6/1996 | Takahasi et al. | 204/603 |
| 5,567,294 | 10/1996 | Dovichi et al. | 204/603 |
| 5,582,705 | 12/1996 | Yeung et al. | 204/603 |

OTHER PUBLICATIONS

Page VI/460 of "Polymer Handbook, 3rd Ed.", ed. Brandrup et al., John Wiley & Sons, 1989 month unknown.
Kambara et al. ("Multiple–sheatflow capillary array DNA analyser", Nature, 361(11), 565–566), Feb. 1993.
Huang et al. ("Capillary Array Electrophoresis Using Laser–Excited Confocal Fluorescence Detection", Anal. Chem. 64(8), 967–9720, Apr. 1992.
Takahashi et al. (Multiple Sheath–Flow Gel Capillary–Array Electrophoresis for Multicolor Fluorescent DNA Detection, Anal. Chem., 66(7), 1021–1–26), Apr. 1994.

*Primary Examiner*—Robert Warden
*Assistant Examiner*—Alex Noguerola
*Attorney, Agent, or Firm*—Antonelli, Terry, Stout & Kraus, LLP

[57] ABSTRACT

A capillary electrophoresis system comprising a plurality of capillaries filled with a migration medium in which samples to which fluorephore labels are added migrate, a light source providing an excitation light exciting the fluorephore labels, a photo detector detecting a fluorescence radiated from the fluorephore labels, and light focusing means placed between the plurality of capillaries to which the excitation light is irradiated. The parts of the plurality of capillaries to which the excitation light is irradiated and the light focusing means are arranged in a plane shape. The excitation light is irradiated through the plurality of capillaries and the light focusing means, the capillaries and light focusing means alternatively placed in the parts where an excitation light is irradiated. The light focusing means consisting of cylindrical rod lenses. The axis of the cylindrical rod lenses is placed substantially parallel with the capillaries, which can detect the fluorescence from samples by irradiating a plurality of capillaries substantially at the same time in a batch without mechanical scanning of a plurality of capillaries or without optical scanning of a light beam, providing a highly sensitive detection of samples.

25 Claims, 9 Drawing Sheets

FIG.10B

CAPILLARY ARRAY ELECTROPHORESIS SYSTEM

BACKGROUND OF THE INVENTION

The present invention relates to an analysis system for DNA, RNA or proteins, etc., and more particularly to a capillary array electrophoresis system which performs sequencing DNA and RNA or detection of polymorphism of restriction endonucleases.

BACKGROUND OF THE INVENTION

With the advancement of a genome project, etc., analysis of biological substances including DNA is becoming important. Gel electrophoresis is used for the analysis of these biological substances. Voltage is applied to a slab gel formed between two glass plates to migrate DNA, etc. in the gel and to separate by size. Recently, a DNA sequencer, etc., which are apparatuses to perform a real-time detection of fluorephore labeled samples such as DNA in migration, are commercially available and widely used. On the other hand, a capillary array electrophoresis system using plurality of fused silica capillaries with ID of around 0.02 to 0.1 mm filled with a separation medium and arranged instead of a slab gel has been developed as an apparatus which is more convenient and which can realize a high speed and a high throughput (Nature 361 (1993) 565–566).

In a fluorescence detection system, the angle made by the direction of the light from a light source (a laser is often used) irradiating the migrating samples and the direction receiving the fluorescence from a fluorescent substance labeling the samples is the right angle because the background light such as scattered light can be lessened. In a capillary array, many capillaries are arranged to detect the DNA, etc. migrating in the capillaries, a detector counterposed to the plane on which capillaries are arranged so as to detect the light from all the capillaries simultaneously.

As methods to irradiate the light for exciting the fluorescent substance labeling the samples, there are the typical methods below: In the first conventional technique, excitation lights are scanned on the capillary array to irradiate DNAs migrating in every capillary (Reference: Anal. Chem. 64, (1992) 967–972). In the second conventional technique, DNAs are eluted from the capillaries into buffer solutions and a light is irradiated from a direction perpendicular to the migration lines and parallel with the plane on which the migration lines are arranged to irradiate the DNAs migrating in buffer solutions (U.S. Pat. No. 5,529,679).

The excitation light is not directly irradiated to a plurality of capillaries because not all the capillaries are irradiated simultaneously since the light is scattered or reflected by some initial capillaries (Reference: Anal. Chem. 66, (1994) 1021–1026).

SUMMARY OF THE INVENTION

In the first conventional technique above, there were problems in that light irradiation time for a migration line was so short that sufficient quantity of light is hardly received and in that the detector easily fails because of mechanical scanning. In the second conventional technique described above which suggested a sheath-flow method in which buffer solutions were flown lest components separated in the buffer solutions diffuse and commingle, there were problems in that it was apt to invite reduction of sensitivity because the samples such as DNAs eluted from the capillaries into the sheath-flow were diluted to reduce sample concentration at the position to detect the samples.

There was another problem in the sheath-flow method that it was not suitable for systems using replaceable (polymer) gels because of its requirement for preparation of a sheath-flow-cell and a capillary array holder. This was so because the replaceable gel would flow out from the capillary ends into the sheath-liquid or the systems would become complex owing to necessity of replacing operation through the sheath-flow-cell.

It is an object of the present invention to provide a capillary array electrophoresis system which can make a laser irradiate a plurality of capillaries substantially at the same time and detect fluorescence radiated from fluorophore labeled sample components migrating in respective capillaries substantially at the same time in a batch, performing on-column fluorescence detection, without mechanical scanning of a plurality of capillaries, or without optical scanning of a light beam, so as to solve the problems of the prior art described above.

To solve the problems described above, in the present invention, in a method where a laser is irradiated through capillaries to a part where polyimide coating near migration ends of the capillaries in which samples migrate is removed to detect fluorescence, many capillaries and lenses are arranged alternately in a plane shape or capillaries and lenses mixed in a prescribed order are arranged in a plane shape and incidence of a laser is made to pass through plurality of capillaries and lenses substantially at the same time along the plane formed by the capillary array to irradiate all in a batch. Surroundings of the position to irradiate a laser light where a fluorescence radiates, with the laser irradiation, from a fluorophore which labels samples, are filled with substances such as water which have a refractive index close to that of glass and the position to irradiate the laser light are irradiated by the laser.

When many capillaries are irradiated in series with one laser, the irradiated laser attenuates every time it passes through a capillary. This is attributed to two causes: (1) reflection of the laser on the interface and (2) divergence of the light owing to a lens action of the capillaries which allows the light to escape out of the capillaries.

A capillary acts like a convex lens while the gel in the capillary acts as a concave lens, resulting divergence of a laser. But then again, all the capillaries can be irradiated substantially at the same time without deviating the laser from neighborhood of central axis of many capillaries by arranging lenses between the arrayed capillaries to suppress the divergence of a laser. Furthermore, reflection on the interface can be far more lessened than putting in a gaseous phase and the divergence of a laser can be practically ignored by soaking the capillaries and lenses into a liquid such as water.

To describe the present invention more specifically, the capillary electrophoresis system of the present invention comprises a plurality of capillaries filled with migration media in which fluorephore labeled samples migrate, a light source providing an excitation light to excite fluorophore labels, a light detector detecting a fluorescent light radiated from the fluorophore labels, and light focusing means arranged between a plurality of capillaries irradiated by the exciting light, wherein the positions of plurality of capillaries and light focusing means which are irradiated by the exciting light are arranged in a plane shape and wherein the excitation light is irradiated through a plurality of capillaries and the light focusing means.

The capillary electrophoresis system of the present invention is characterized as follows:

(1) Capillaries and light focusing means are arranged alternately in a position irradiated by an excitation light.

(2) The light focusing means comprise cylindrical rod lenses, the axis of the cylindrical rod lenses arranged substantially parallel with the axis of the capillaries.

(3) The light focusing means comprise capillaries whose inside is filled with a liquid or a solid.

(4) The light focusing means comprise spherical lenses or globular lenses arranged on an irradiation axis of the excitation light.

(5) The positions of plurality of capillaries and light focusing means which are irradiated by the exciting light are arranged in a liquid such as water.

(6) An antireflection coating is formed on the outside surface of at least the positions of plurality of capillaries and light focusing means which are irradiated by the exciting light.

More concretely, the capillary electrophoresis system of the present invention is characterized in that they have following constructions:

(a) A construction comprising a plurality of quartz capillaries filled with a migration medium, made up of a polymer with 1.40 or a higher refractive index, in which fluorophore labeled samples migrate, a light source providing an excitation light to excite fluorophore labels, and a light detector detecting a fluorescent light radiated from the fluorophore labels, wherein the positions of plurality of capillaries which are irradiated by the exciting light are arranged in a plane shape and placed in water and wherein the excitation light is irradiated through a plurality of capillaries.

(b) A construction comprising a plurality of quartz capillaries filled with a migration medium, made up of a polymer with 1.40 or a higher refractive index, in which fluorophore labeled samples migrate, a light source providing an excitation light to excite fluorophore labels, a light detector detecting a fluorescent light radiated from the fluorophore labels, and light focusing means arranged between a plurality of capillaries, wherein the positions of plurality of capillaries and the light focusing means which are irradiated by the exciting light are arranged in a plane shape and placed in water and wherein the excitation light is irradiated through a plurality of capillaries and light focusing means.

(c) A construction comprising a plurality of quartz capillaries filled with a migration medium, made up of a polymer with 1.40 or a higher refractive index, in which fluorophore labeled samples migrate, a light source providing an excitation light to excite fluorophore labels, a light detector detecting a fluorescent light radiated from the fluorophore labels, and light focusing means periodically arranged every six or less capillaries, wherein the positions of plurality of capillaries and the light focusing means which are irradiated by the exciting light are arranged in a plane shape and placed in water and wherein the excitation light is irradiated through a plurality of capillaries and light focusing means.

(d) A construction comprising a plurality of quartz capillaries filled with a migration medium, made up of a polymer with 1.38 or a higher refractive index, in which fluorophore labeled samples migrate, a light source providing an excitation light to excite fluorophore labels, a light detector detecting a fluorescent light radiated from the fluorophore labels, and light focusing means periodically arranged every five or less capillaries, wherein the positions of plurality of capillaries and the light focusing means which are irradiated by the exciting light are arranged in a plane shape and placed in water and wherein the excitation light is irradiated through a plurality of capillaries and light focusing means.

(e) A construction comprising a plurality of quartz capillaries filled with a migration medium, made up of a polymer with a refractive index within a range from 1.36 to 1.41, in which fluorophore labeled samples migrate, a light source providing an excitation light to excite fluorophore labels, a light detector detecting a fluorescent light radiated from the fluorophore labels, and light focusing means arranged in alternation with capillaries, wherein the positions of plurality of capillaries and the light focusing means which are irradiated by the exciting light are arranged in a plane shape and placed in water and wherein the excitation light is irradiated through a plurality of capillaries and light focusing means.

Also, the capillary electrophoresis system of the present invention (f) comprises a plurality of capillary arrays consisting of a plurality of capillaries which are filled with a migration medium in which fluorephore labeled samples migrate and whose migration ends are arranged in a plane shape, a light source radiating an excitation light which excites fluorophore labels outside the migration ends of the respective plurality of capillaries in a plurality of capillary arrays, a light detector which detects the fluorescence radiated from the fluorophore labels, and convex lenses arranged on the optical axis irradiated by the exciting light in a space to which, said respective plurality of capillary arrays are extended, which irradiates the external of the migration ends (sheathflows formed near the migration ends), or (g) comprises a plurality of capillary arrays consisting of a plurality of capillaries which are filled with a migration medium in which fluorephore labeled samples migrate, a plurality of capillary arrays consisting of light focusing means arranged between a plurality of capillaries at the ends of a plurality of capillaries, a light source radiating an excitation light which excites fluorophore labels at respective ends of a plurality of capillary arrays, a light detector which detects the fluorescence radiated from the fluorophore labels, wherein respective ends of a plurality of capillary arrays and light focusing means which are irradiated by the exciting light are arranged in a plane shape and laminated and wherein the excitation light is irradiated through a plurality of capillaries and the light focusing means in respective laminated layers.

According to the present invention, a laser beam which irradiates a plurality of capillaries in a batch is condensed by the lenses placed in the capillary arrays, efficiently exciting samples migrating in a plurality of capillaries to improve detection sensitivity. It is possible to prevent the more reduction of laser intensity and sensitivity caused by reflection, refraction when a plurality of capillaries are arranged on a plane and a laser is irradiated to pass through a plurality of capillaries along the plane substantially at the same time.

Figure 2:
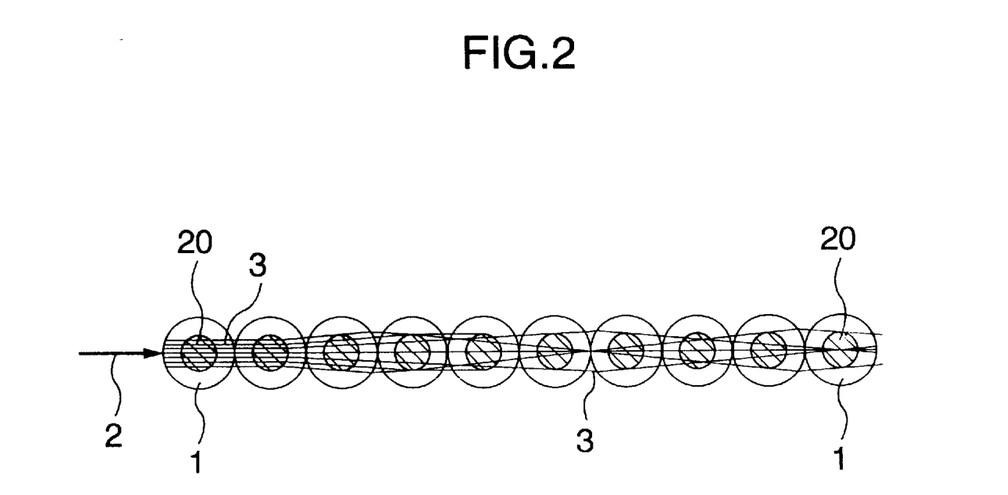
FIG. 2 is a diagram illustrating the results of simulation of the laser paths through capillaries when the capillary arrays of FIG. 1 are placed in water.
Figure 3:
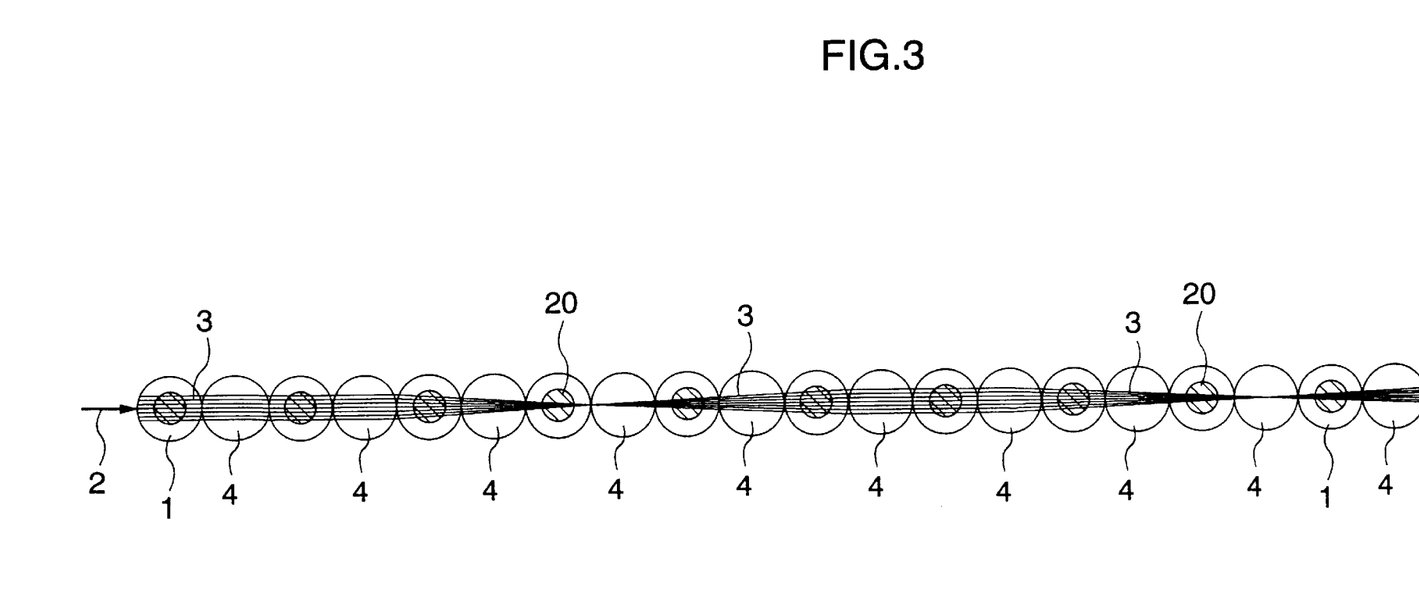
FIG. 3 is a diagram illustrating the results of simulation of the laser paths when rods made of quartz are arranged between respective capillaries of FIG. 1 and placed in water.

The present invention will be summarized below using FIG. 3. FIG. 3 shows the results of simulation of a laser path in a case where quartz glass cylindrical rods (whose OD is the same as that of the quartz capillaries 1) as the rod lenses 4 arranged between the arrays of the quartz capillaries 1 and placed in water are irradiated by the laser 2. Most of the laser 2 passes in the gel 20. By the construction of the present invention, about 5 times numbers of capillaries can be irradiated by the laser as compared with a case where 10 capillaries are arranged in air. Instead of rod lenses whose section is a circle, convex lenses, spherical lenses, convex lenses in a rod shape and the like may be used, and instead of the quartz glass rods 4, quartz capillaries filled with a liquid having a refractive index close to that of glass may also be placed, the quartz capillaries filled, for example, with formamide (refractive index: 1.45). As a result, a capillary array electrophoresis system can be realized without mechanically scanning a plurality of capillaries and optically scanning light beams, which irradiates a plurality of capillaries substantially at the same time to detect fluorescent lights from samples and can detect samples with a high sensitivity, using more capillaries.

DESCRIPTION OF THE PREFERRED EMBODIMENTS

Examples of the present invention will be described in detail below using figures.

(First example)

Figure 1:
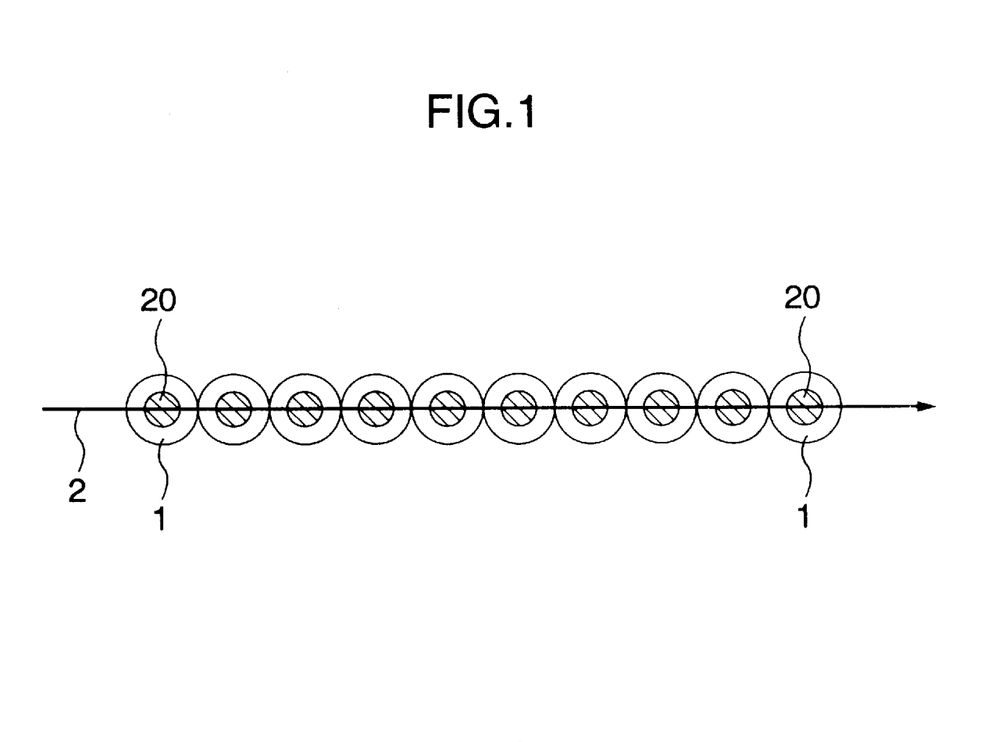
FIG. 1 is a cross-sectional view of the position of the capillary array where a laser is irradiated which is the first example of the present invention.

FIG. 1 is a cross-sectional view of the position of the capillary array where a laser is irradiated, illustrating the first example of the present invention (the over coat of the capillaries are removed, of course). As shown in FIG. 1, a laser 2 is irradiated from a direction parallel with the plane made by the capillary array to the capillary array in which ten capillaries 1 whose inside is filled with the gel 20 are arranged in a plane shape so that the laser can pass through the ten capillaries substantially at the same time. The refractive indices of air, capillary material, gel and water here are respectively 1.00, 1.46, 1.36 and 1.33.

If the laser irradiation positions on the capillary arrays are placed in air to irradiate the laser, the reflectance on the interface between the air and the glass is about 4%, leading to a conclusion that 8–9% of the irradiated light per a capillary is reflected (including reflectances on outside and inside of the capillary). On the other hand, if the laser irradiation positions are placed in water to irradiate the laser, the reflectance per interface is lower by one order of magnitude and ca. 1.5% attenuation of the irradiated light per passing one capillary having four interfaces in total occurs. If a laser is irradiated to ten capillaries placed in air, the irradiation intensity at the tenth capillary is about 35% of the irradiation intensity at the first capillary ($0.9^{10}=0.35$ when the attenuation of the irradiated light per a capillary is 10%).

On the other hand, assuming that a laser irradiated in water does not diverge due to refraction caused by capillaries, the irradiation intensity at the tenth capillary is about 86% of the irradiation intensity at the first capillary ($0.985^{10}=0.86$ when attenuation of the irradiated light per a capillary is 1.5%). The intensity of a laser irradiation to 70th capillary when the laser is irradiated to about 70 capillaries placed in a plane is about 35% of the irradiation intensity at the first capillary ($0.985^{70}=0.35$ when attenuation of the irradiated light per a capillary is 1.5%), showing that losses of light in water owing to reflection are by far fewer. However, in water the light is diverged by the capillaries.

FIG. 2 shows the results of simulation of an optical path of a laser passing capillaries when a capillary array of ten capillaries with 0.2 mm of OD and 0.1 mm of ID filled with a gel is placed in water. Similar to FIG. 1, FIG. 2 shows an optical path 3 along which the laser 2 proceeds when the laser 2 is irradiated from a direction parallel with a plane made by a capillary array to the capillary array consisting of ten capillaries 1 whose inside is filled with the gel 20 arranged in a plane shape so that the laser can pass through the ten capillaries substantially at the same time. As evident from FIG. 2, the laser often passes not the part of the gel 20, indicating that sufficient intensity of the laser is not irradiated to the part of the gel. This is so because the refractive index of the gel in the capillaries is about 1.36 which is lower than 1.46, the refractive index of glass, and the gel acts as a concave lens. Of course, the external wall part of the capillaries 1 acts as a convex lens, but the capillaries containing the gel as a whole act as concave lenses because they are surrounded by water (refractive index: 1.33) and they do not condense the light.

Next, a construction which irradiates a sufficient intensity of a laser to the part of the gel of the capillary array is described. In this example, a cylindrical glass rod (made of quartz as a capillary is, with OD 0.02 mm as of a quartz capillary) is used and arranged between the capillaries to condense the laser.

FIG. 3 shows the results of simulation of an optical path of a laser when ten quartz capillaries with 0.2 mm of OD and 0.1 mm of ID whose inside is filled with a gel are used as analyzer tubes and rods of quartz (refractive index: 1.46) with 0.2 mm of OD are arranged between respective capillaries and placed in water. This means that ten capillaries 1 and ten glass rods 4 are alternately placed in water. As evident from the results shown in FIG. 3, most of the laser 2 which enters into the capillary array are shown to pass through the gel 20. The diameter of the glass rods is the same as that of the capillaries in this case, but they may be thicker. However, the same thickness is convenient because it is necessary to put the rod lenses and the capillaries with their central parts coaxial.

Similar effects are obtained when quartz capillaries filled with a liquid with a refractive index close to that of quartz glass are placed instead of the quartz rods. For instance, inside of the capillaries may be filled with formamide (refractive index: 1.45). In other words, the capillaries may be used with their inside filled with formamide instead of the gel. In the case of glass rods, there are two interfaces, one in the incoming side and the other in the outgoing side, which is half of the number of interfaces in the case of capillaries. That is, when a light loss due to reflection on an interface is considered, two glass rods provide a loss equivalent to that of one capillary. For example, in a case where a laser is irradiated to about 48 quartz capillaries and a capillary array of quartz capillaries and quartz glass rods with the same OD placed between them (47 in total) in water, the intensity of light irradiated to the 48th quartz capillary is about 34% of the intensity of the laser irradiated to the first quartz capillary ($0.985^{72}=0.34$ when attenuation of an irradiated light per a capillary is 1.5% and the laser passes through an array equivalent to 72 {48+(47/2)} quartz capillaries), substantially equal to the intensity of the laser irradiated to the tenth quartz capillary when the capillary array is placed in air.

In other words, it is found that about 5 times as many capillaries as in the case where 10 capillaries are arranged in air can be irradiated with a laser by a construction having a capillary array placed in water and quartz glass rods (rod lenses) placed between the quartz capillaries. It goes without saying that the use of convex, spherical, rod-shaped convex lenses and the like instead of the rod-shaped lenses with a circular cross section (rod lenses) allows similar effects.

Furthermore, as described in detail in FIG. 6 later, in cases where migration media (polymers) whose refractive index is appropriately selected are used, the intensity of laser irradiated to a plurality of quartz capillaries can be made sufficient for exciting fluorephores labeling samples to detect fluorescence without using rod lenses. For instance, there is no need to use rod lenses if a polymer with 1.40 or a higher refractive index is used, then the optical path of the laser is, as shown in FIG. 3, narrower than the divergence of an optical path of a laser shown in FIG. 2, allowing substantially complete irradiation of the polymer.

Figure 4:
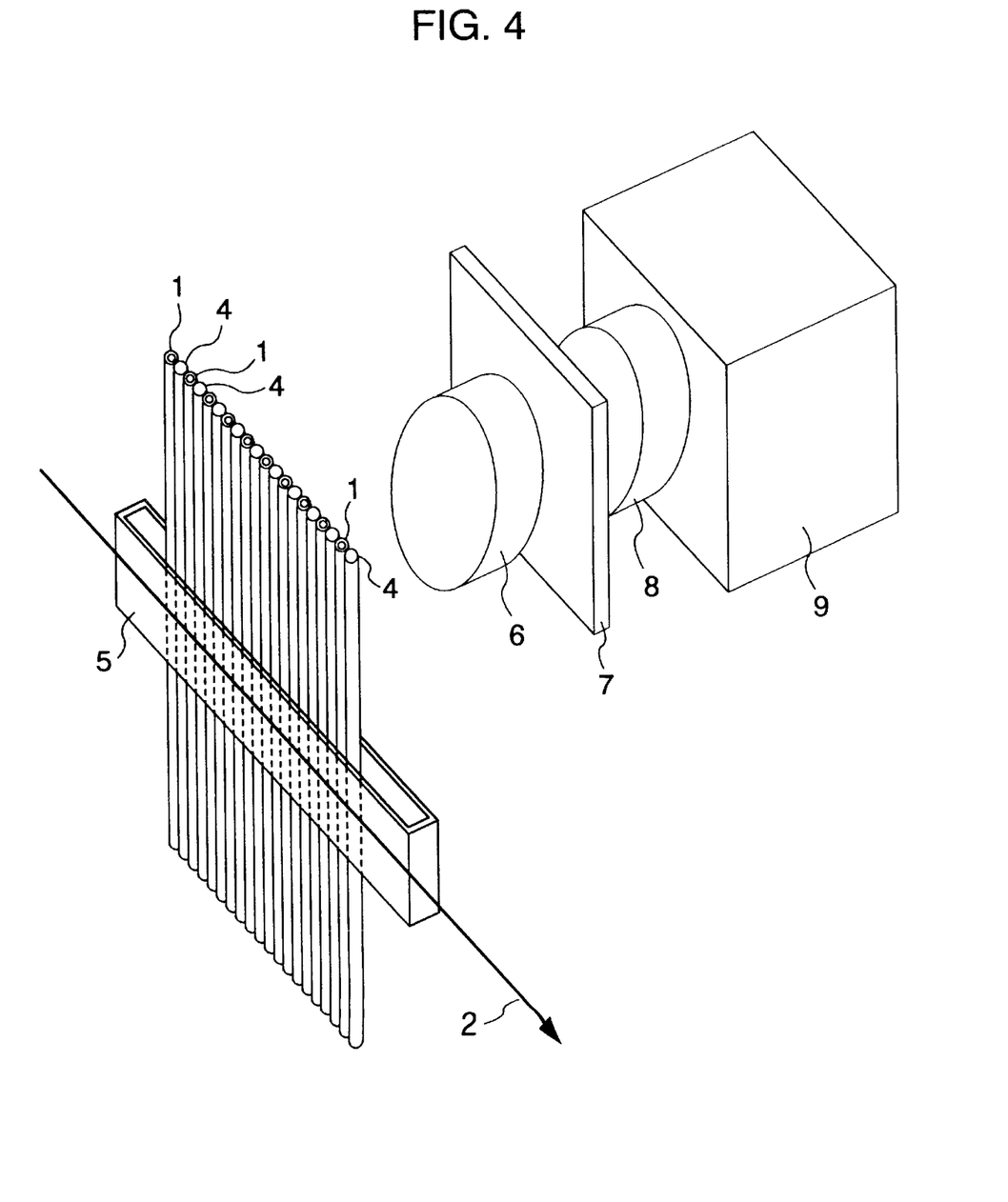
FIG. 4 is a diagram illustrating an outlined construction of a capillary array fluorescence detection system (DNA sequencer) using the capillary array of Example 1.

FIG. 4 is a diagram illustrating an outlined construction of a capillary array fluorescence detection system (DNA sequencer) using the capillary array of the example. In the capillary array shown in FIG. 4, capillaries and glass rods are fixed in a fluorescence cell and a laser is irradiated. As similar to FIG. 3, ten capillaries 1 with 0.2 mm of OD and 0.1 mm of ID and ten quartz glass rods (rod lenses) 4 with 0.2 mm of OD are alternately placed. The quartz capillaries 1 and the quartz glass rods 4 are held in water in a form their laser irradiation positions are sandwiched by transparent glass plates in the optical cell 5. The laser irradiation positions are parts of the capillaries whose protective covering is removed. The laser 2 is irradiated parallel with the plane made by the capillary array so that the laser can pass through the quartz capillaries 1 and the quartz glass rods 4 and the fluorescence from the fluorephore labeling the samples which pass through the laser irradiation positions is detected. Both ends of respective capillaries are soaked into a buffer solution (not illustrated in FIG. 4) and an electric field is applied. The laser is irradiated from a side so that it can pass through respective central axes of the capillary array and rod lenses at the laser irradiation positions.

Samples such as DNAs migrate in the gel packed in the capillaries. The fluorescence radiated from the fluorephore labeling the DNAs passing through the laser irradiation positions passes through the condenser lens 6, the filter 7 and the image-formation lens 8 and imaged on an array sensor (such as a one-dimensional or two-dimensional CCD camera 9) and detected from a direction perpendicular to a plane made by the capillary array. To detect DNAs labeled by various kinds of fluorephores, the image-splitting prism already reported (Anal. Chem. 66(1994)1021–1026) and a plurality of filters or a wheel filter may be used.

Figure 5:
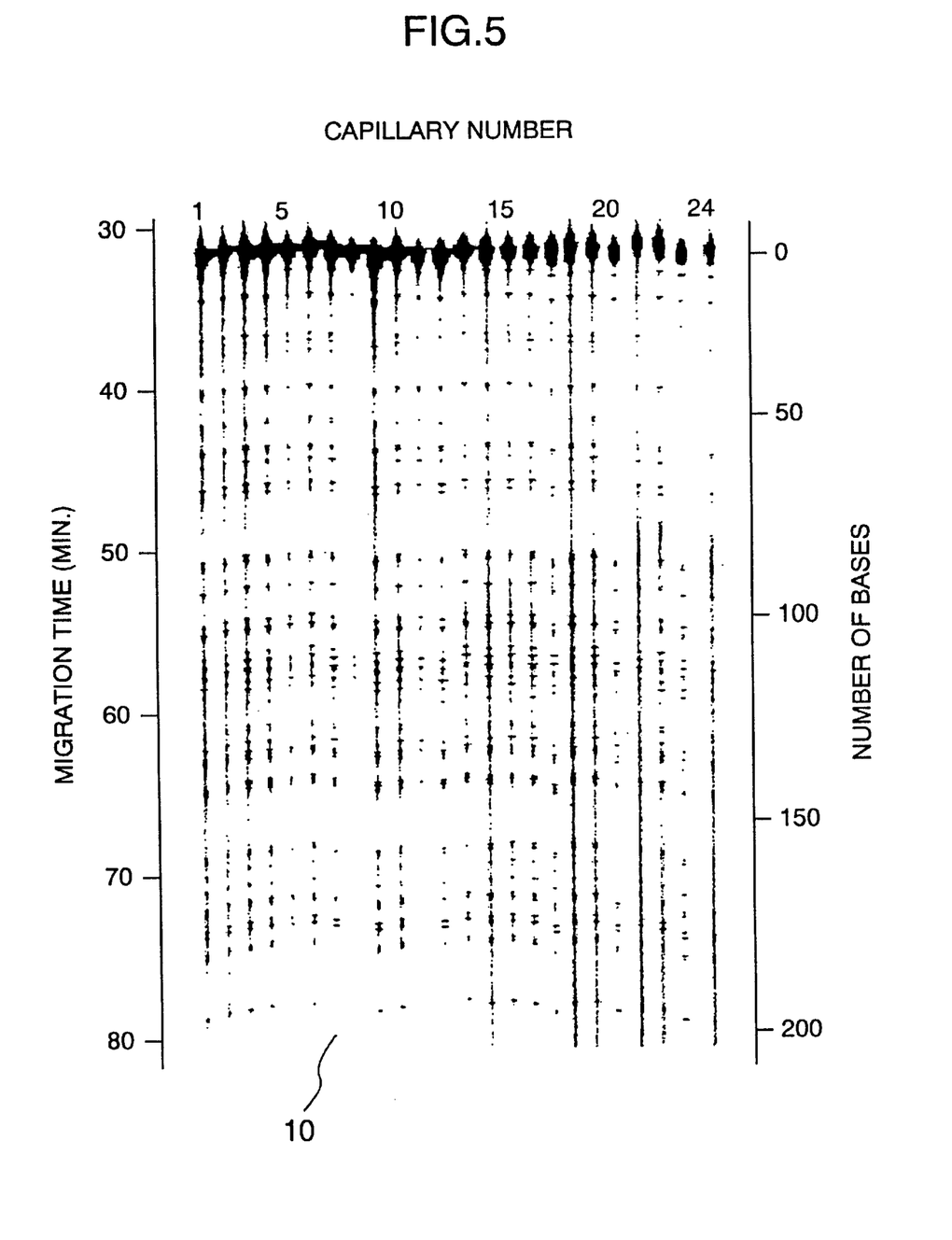
FIG. 5 is a pictorial view illustrating an example of fluorescence signals detected using 24 capillary array gels.

FIG. 5 illustrates an example of fluorescence signals detected using 24 capillary gels in a construction illustrated in FIG. 4. In FIG. 5, the abscissas corresponds to positions of 24 capillaries and represents capillary number counted from the laser entrance position, the left ordinate representing migration time of electrophoresis (min) and the right ordinate 12 representing base length of DNA. Since fluorescence signal 10 (concentration of the image represents the fluorescence intensity) are weakened as the capillary number in FIG. 5 increases (as they distance from the laser source), FIG. 5 shows the results of compensation of the intensity so that the fluorescence signals from each capillary may have substantially the same intensity for the sake of clearness. With the construction of the example, detection can be independently performed without influence of shapes of capillary ends owing to the on-column detection whose laser irradiation passes through the capillaries.

In cases where a polymer gel is used, fluorescence detection is not affected at all even if the polymer slowly flows out from the capillary ends into the buffer solution so long as the laser irradiation positions are apart from the capillary ends in a degree not to influence on the laser irradiation positions. A polymer gel is convenient because it is ejected by pressure and substituted with a new gel, repetitively using a capillary, and it is also advantageous for full automatization of the system.

Figure 6:
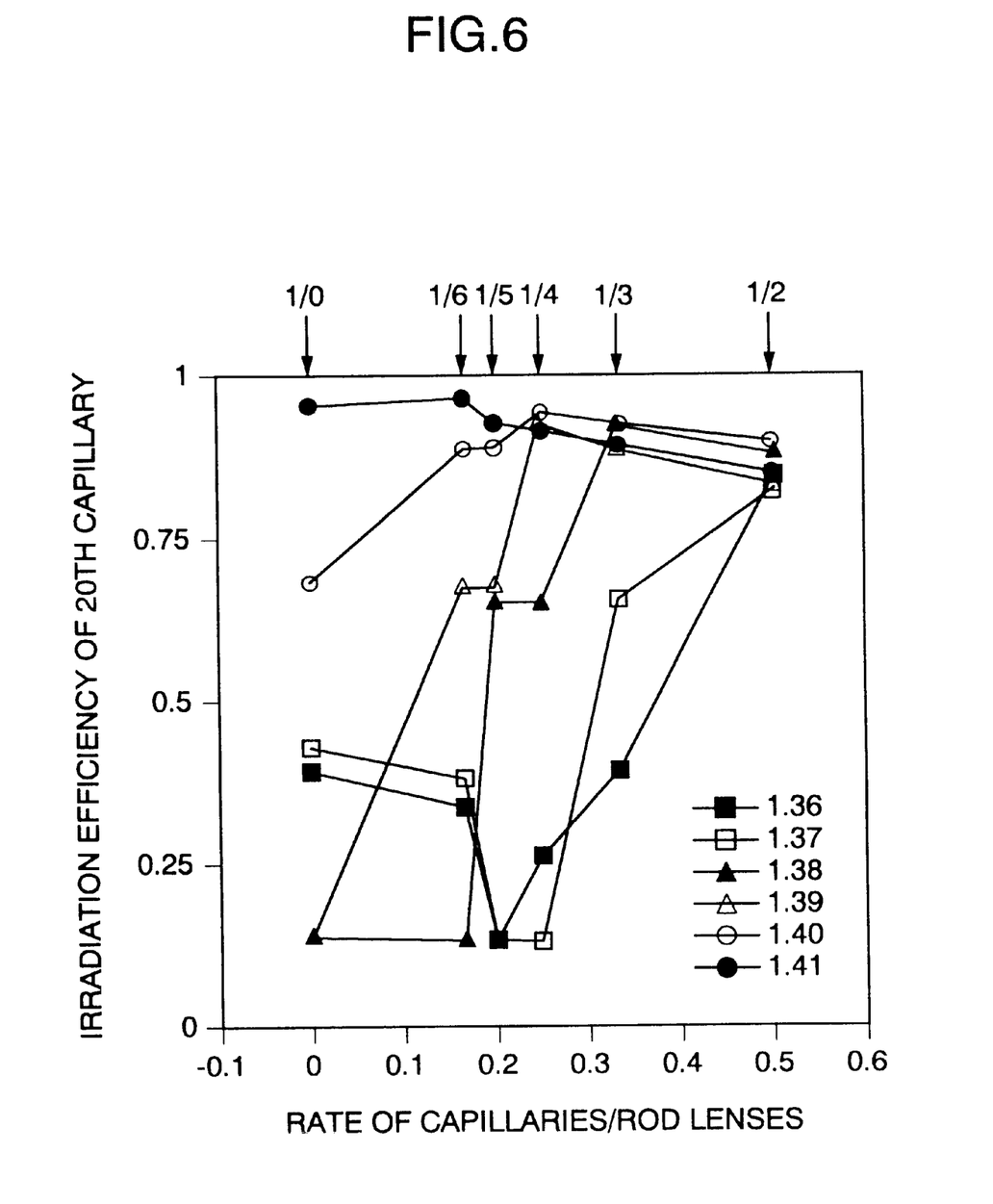
FIG. 6 is a graph showing the results of investigation of influence of refractive indices of a migration medium for separation in the construction of Example 1.

FIG. 6 is a graph showing the results of investigation of influence of refractive indices of a migration medium for separation in the construction of the example described above. FIG. 6 shows the relationship between the conditions of combination of 20 quartz capillaries with rod lenses and the laser irradiation efficiency of 20-th quartz capillary (the laser irradiation intensity of 20-th quartz capillary/the laser irradiation intensity of 1st quartz capillary), when the construction of acrylamide (refractive index: 1.36) described above is changed and used with rod lenses placed in water, using 6 kinds of migration media (■, □, ▲, △, ○ and ●) having different refractive indices ranging from 1.36 to 1.41, the rod lenses having the OD and refractive index which are the same as those of the quartz capillaries . The ordinate of FIG. 6 represents irradiation efficiency of 20-th capillary and the lower abscissa represents glass capillary rates in periodical arrangement of quartz capillaries and rod lenses.

The upper abscissa of FIG. 6 indicates the ratio in the periodical arrangement of quartz capillaries and rod lenses, the ratio=the number of the rod lens (=1)/the number of quartz capillaries (=N), meaning that one rod lens is placed against N quartz capillaries. N=0 is the case where no rod lens is used (corresponding to FIG. 1).

The results of FIG. 6 indicate that the use of a migration medium (polymer) whose refractive index is properly selected also allows to make the quantity of the laser irradiated to a plurality of quartz capillaries sufficient for exciting the fluorephore labeling samples and for detecting its fluorescence without using a rod lens. Evaluation of the quantity of the laser irradiation with the irradiation efficiency of 20-th quartz capillary leads to the following conclusions:

(1) When a polymer with 1.40 or a higher refractive index is used (○, ●), the irradiation efficiency of the laser >0.65 can be attained without necessity to use a rod lens.

(2) When a polymer with 1.40 or a higher refractive index is used (○, ●), combination of 6 or less quartz capillaries to a rod lens and periodical placement allow to attain the irradiation efficiency of the laser >0.85.

(3) When a polymer with 1.38 or a higher refractive index is used (▲, △, ○, ●), combination of 5 or less quartz capillaries to a rod lens and periodical placement allow to attain the irradiation efficiency of the laser >0.65.

(4) When the refractive index is within a range from 1.36 to 1.41, arranging a rod lens and a quartz capillary alternately allows to attain the irradiation efficiency of the laser >0.80.

(Second example)

Figure 7A:
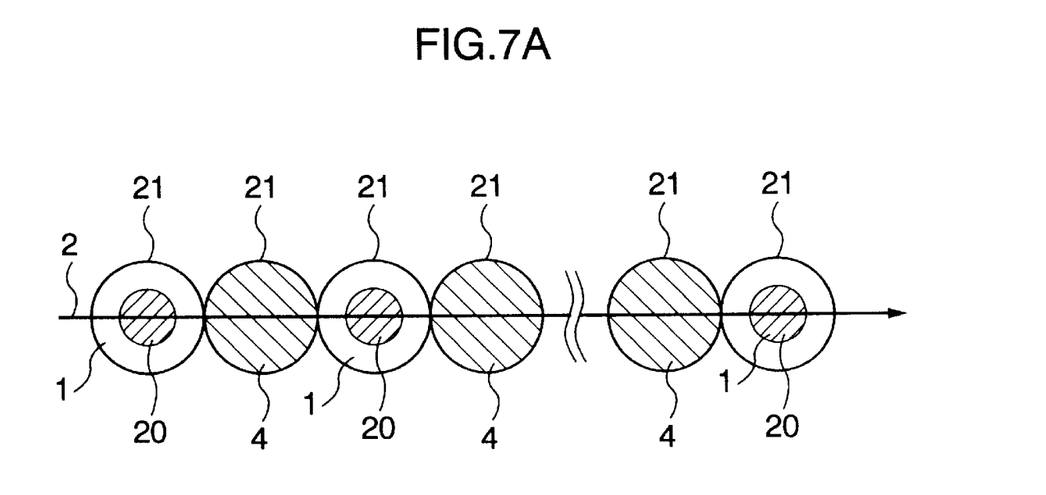
FIGS. 7A and 7B are diagrams illustrating the second example of the present invention in which a reflection prevention membrane is formed on the external of capillaries and lenses to construct capillary arrays to which a laser is irradiated in air, the reflection prevention membrane is formed on all the peripheries of the capillaries and lenses in FIG. 7A and on parts of the periphery of the capillaries and lenses in FIG. 7B.
Figure 7B:
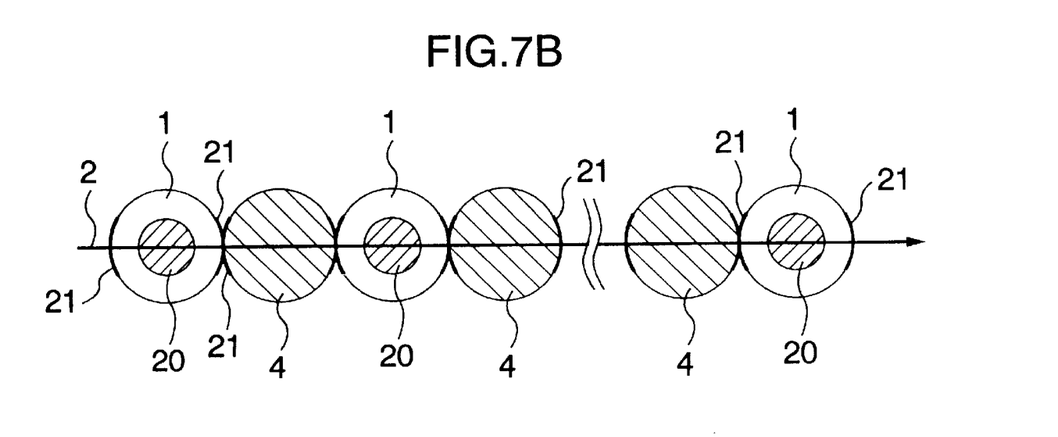

FIGS. 7A and 7B show examples in which a capillary array is constructed, with reflection reducing coatings formed on the external surface of the capillaries and on the external surface of the lenses instead of soaking the capillaries and lenses in water to irradiate a capillary array in air. FIG. 7A shows an example forming reflection reducing coatings on all the peripheries of the capillaries and lenses at the position where a laser is irradiated. FIG. 7B shows an example forming reflection reducing coatings on parts of the peripheries of the capillaries and lenses at the position where a laser is irradiated. The reflection on the surface of a capillary can be reduced to about 0.5% by forming the reflection reducing coatings. As a result, the loss of the laser on passing through a capillary is about 1%, and many capillaries can be irradiated in a batch at the same time because the intensity of the laser is about 36%, strong enough, after passing through 100 capillaries. It may be enough if the reflection reducing coatings 21 are formed at least the circumferential surfaces of the capillaries 1 and lenses 4 (for which quartz glass rods having an OD the same as that of the capillaries 1 are used) facing the optical path of the laser. For instance, the reflection reducing coatings 21 may be formed within a range about 90 degrees of counterposed on the peripheries of the capillaries 1 and lenses 4, and the capillaries and lenses may be placed in close contact so that the central parts of the reflection reducing coatings may be placed on the line joining the central axes of the capillaries and lenses.

To form the reflection reducing coatings, respective capillaries are fixed in a rectangular holder and a reflection reducing coating ($MgF_2$ coating, multilayer coating or the like) is deposited from both counterposed sides. The upper and lower sides of surfaces of the capillaries arranged in a plane shape are made to have reflection reducing coatings. Also, reflection reducing coatings may be deposited, holding respective capillaries in an array shape with the distance not less than 2 mm apart, and the deposition part of the reflection reducing coatings of respective capillaries are used in close contact. Of course, reflection reducing coatings may be deposited on all the peripheries of the capillaries, rotating a respective capillaries on a rectangular holder.

As known to the public, a thickness of a single layer reflection reducing coating d is presented by an equation $d=\lambda/(4n)$ in the case of the light with a single wavelength $\lambda$ whose angle of incidence is 0 degree when the wavelength of the laser is $\lambda$, the refractive index of air $n_0=1.00$ and the refractive index of the single layer reflection reducing coating is n. For instance, d=96.4 nm if the refractive index of $MgF_2$ coating n=1.38 and $\lambda$=532 nm. The refractive index of the ideal single layer reflection reducing coating is provided by the square root of $(n_{base})$=1.21 if the refractive index of quartz $n_{base}$=1.46, and if $\lambda$=532 nm, then d=110 nm. Furthermore, in the case of the light with a single wavelength $\lambda$ whose angle of incidence is 0 degree, when the constitution is comprised of air, the first layer, the second layer and quartz, the refractive index of air $n_0=1.00$, the refractive indices of the respective reflection reducing coatings are $n_1$ (the first layer) and $n_2$ (the second layer) and the refractive index of quartz $n_{base}$=1.46, it is only necessary to make the refractive index $n_0$ equal to that of air, 1.00, that is, satisfy the relation $n_0=(n_1^2 \cdot n_{base})/n_2^2$ and make the thickness of the first and second layers $\lambda/4$, to make the reflectance 0. For instance, when the first layer is formed of magnesium fluoride ($MgF_2$; $n_1$=1.38), all you need is selecting a substance with $n_2$=1.67 or close to it as the second layer.

(Third example)

Figure 8:
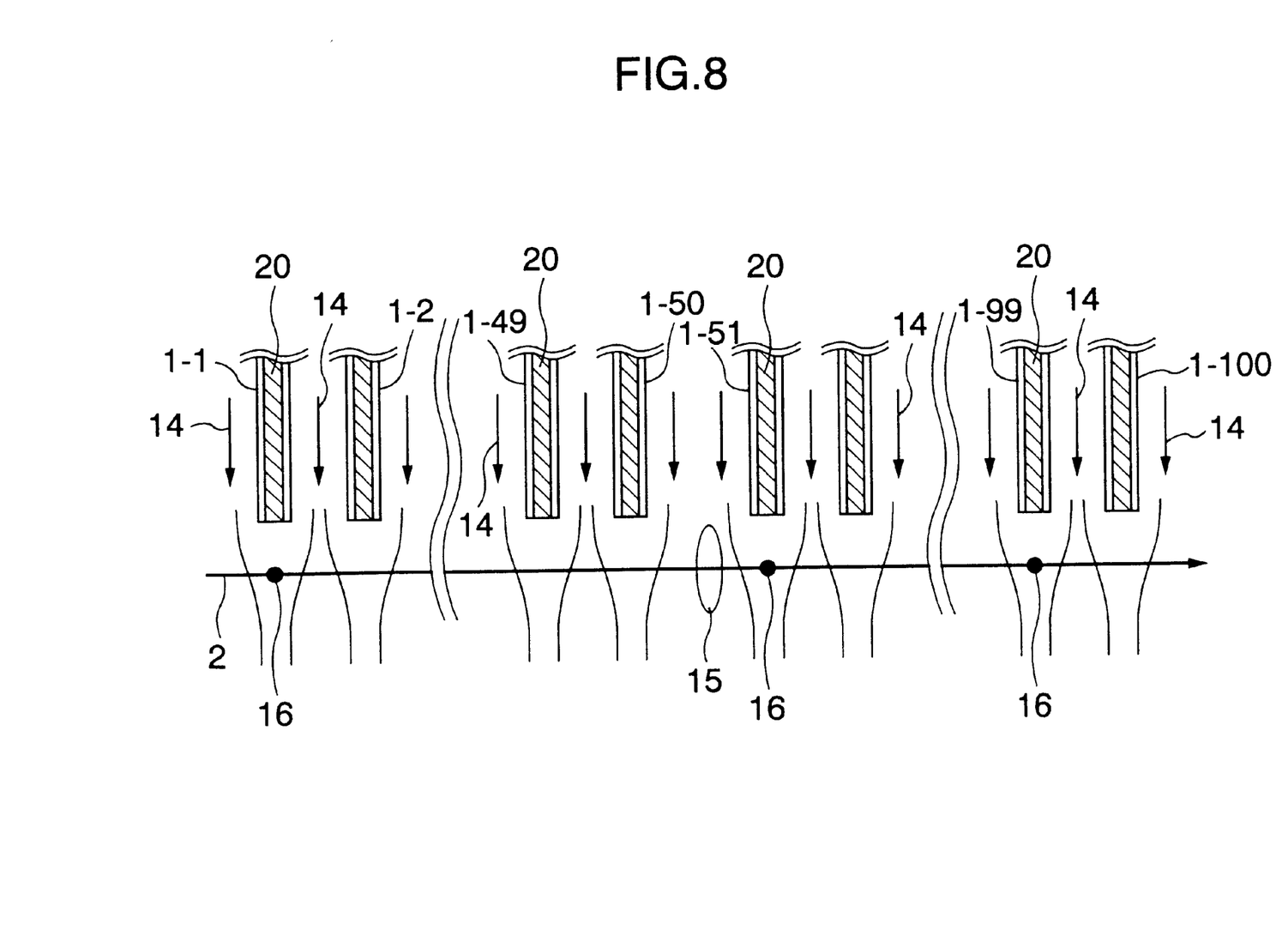
FIG. 8 is a diagram illustrating the third example of the present invention in which convex lenses are arranged with every constant distance in the traveling direction to re-focus a laser when the laser is irradiated in a sheathflow to detect samples.

FIG. 8 is a diagram illustrating the example in which convex lenses are placed in the traveling direction to re-focus a laser when the laser is irradiated in a sheath-flow to detect samples. The construction is effective not only for the case where laser irradiation is performed with passing capillaries but also for the case where biology-related substances migrating in capillaries are extracted from the capillaries and a laser is irradiated to detect them. As in the first example, in the case where a laser is irradiated by passing through capillaries along the plane made by the capillary array, there is a light focusing effect in the direction perpendicular to the axis direction of the capillaries, while there is no lens effect in the longitudinal direction (axis direction of the tubes) and it is difficult to irradiate a long distance with the laser thinly focused. On the other hand, there are the same circumstances in the case where samples such as DNAs separated in capillaries are extracted from the capillaries into a sheath-flow and a laser is irradiated, the laser power does not attenuate very much but samples cannot be irradiated in a thin laser over a long distance. It is therefore effective to place convex lenses to re-focus the laser in the longitudinal and transverse directions. The example shown in FIG. 8 places 100 capillaries (1-1, 1-2, -, 1-100) filled with gel 20 in sheath-flow cell (not shown), irradiates a laser substantially at the same time in a batch to fluorephore-labeled samples 16 eluted from respective capillaries along the flow of the buffer solution 14 and detects the fluorescence from the direction perpendicular to the page plane of FIG. 8 with a fluorescence detection system similar to that shown in FIG. 4. The capillaries are divided into two blocks of 50 capillaries (1-1–1-50; 1-51–1-100) and the convex lens 15 is placed on an axis where the laser is irradiated in the middle of the two blocks to re-focus the laser beam. The lens used is a symmetric convex lens with 20 mm of a focal length. In the construction of the first example, it goes without saying that convex or spherical lenses may be used instead of the rod lenses 4.

In FIG. 8, 100 capillaries are divided into two blocks and the convex lens 15 is placed on an axis where the laser is irradiated in the middle of the two blocks to re-focus the laser beam, while it is also possible, for example, to place 1000 capillaries divided into blocks of 50 capillaries (or 25 capillaries) in the sheath-flow cell (not shown) and to place a lens such as a convex, spherical or rod lens on an axis where the laser is irradiated in the middle of the two blocks so as to re-focus the laser beam.

(Fourth example)

Figure 9A:
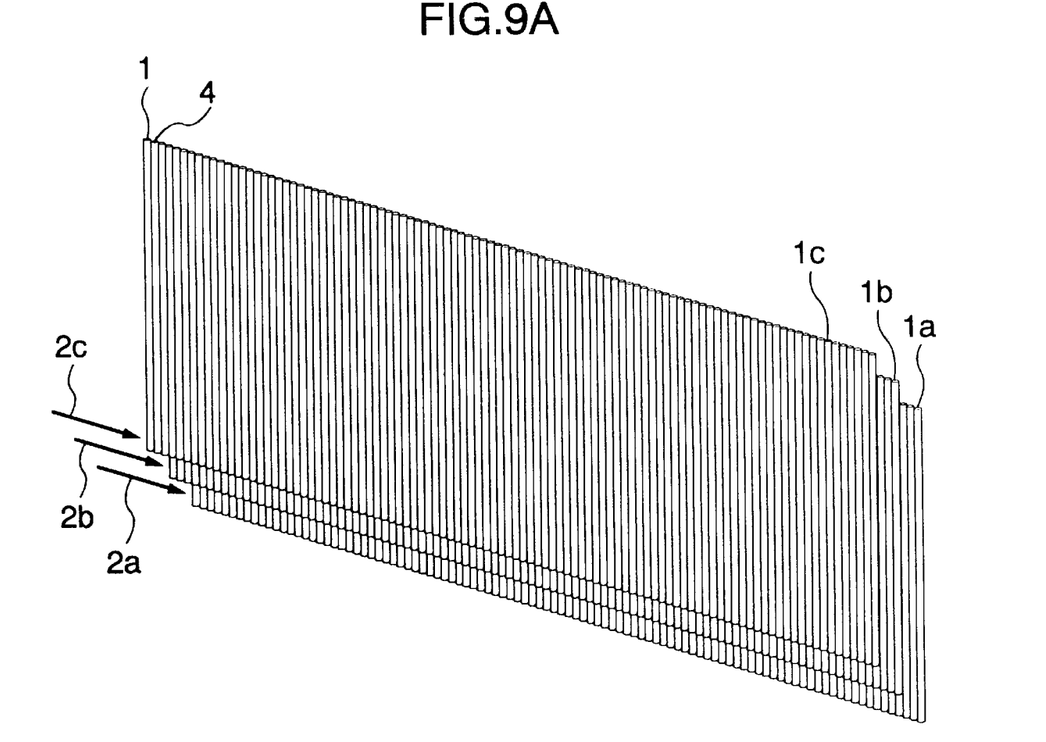
FIGS. 9A and 9B are diagrams illustrating the fourth example of the present invention and an example of construction in which capillary arrays are overlapped and laser irradiation positions are staggered with respective capillary arrays to form multiple fluorescence images which are detected, FIG. 9A being the front view and FIG. 9B being the side view.
Figure 9B:
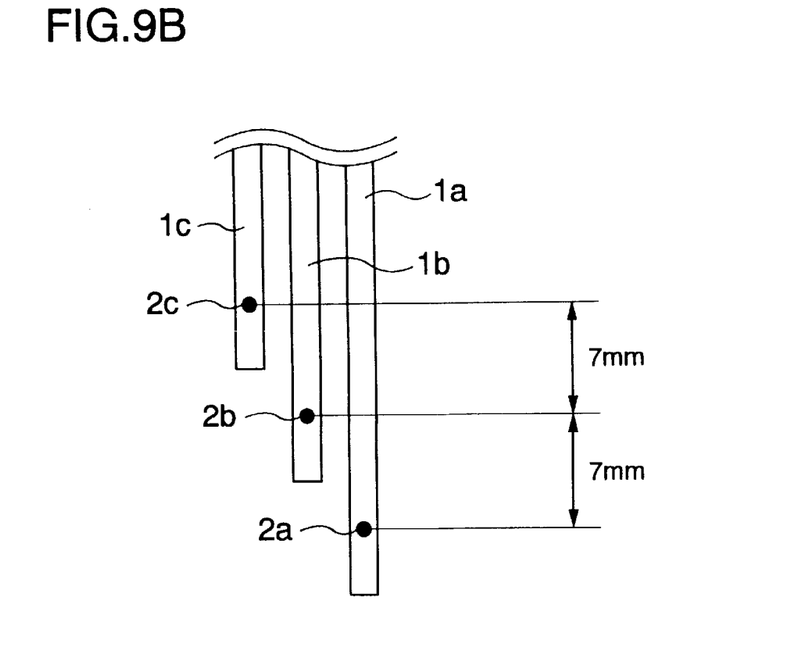

FIGS. 9A and 9B are diagrams illustrating the example of a construction in which capillary arrays are overlapped and laser irradiation positions are staggered with respective capillary arrays to form multiple fluorescence images which are detected simultaneously, FIG. 9A being the front view and FIG. 9B being the side view. Capillary arrays 1a, 1b and 1c are overlapped, and lasers 2a, 2b and 2c are irradiated respectively passing through the capillary arrays 1a, 1b and 1c. If the number of the capillaries are too large, the laser widths become larger as the laser proceeds, and it becomes difficult to detect samples since the irradiation density of the laser is reduced. As a detector to detect the fluorescence, a line sensor or an area sensor is good. However, when a fluorescence image with a long width is attempted to receive, a minified image of the fluorescence image is formed on the detector by an imaging lens, then the quantity of the received light becomes smaller. In this case, as shown in FIGS. 9A and 9B, it is effective to two-dimensionally form a fluorescence image, which is formed at intersections of laser 2a, 2b, 2c and every capillary and to detect with an area sensor (not shown). A capillary array used in FIGS. 9A and 9B is such a capillary array that capillaries (OD: 0.2 mm, ID: 0.1 mm) and glass rods (rod lenses; OD: 0.2 mm) are alternately arranged, 50 of the capillaries and 50 of the rod lenses alternately arranged, with the array width being 20 mm. The capillary array is overlapped to be triplex and placed in water. By staggering laser irradiation positions of respective components in the direction of the capillary axis, fluorescence images are set not to overlap with each other seen from a direction perpendicular to the capillary array. In other words, the fluorescence (fluorescence image) radiated at laser irradiation positions of respective components is detected at the same time from a direction perpendicular to the page plane of FIG. 9A (from the left in FIG. 9B).

The capillary arrays are placed in a buffer solution and a laser is irradiated through the capillaries near the capillary ends. The distance between the laser irradiation positions is about 7 mm. Three fluorescence images (50×3=150 point images) formed at the laser irradiation location are further formed through an image-splitting prism and color filters to make four different color images as 12 linear fluorescence images (150×4=600 point images) on a two-dimensional detector detected in a fluorescence detector system similar to one shown in FIG. 4. Base sequences of 150 DNAs can be determined by analyzing four different fluorescence radiated from 150 capillaries.

(Fifth example)

Figure 10A:
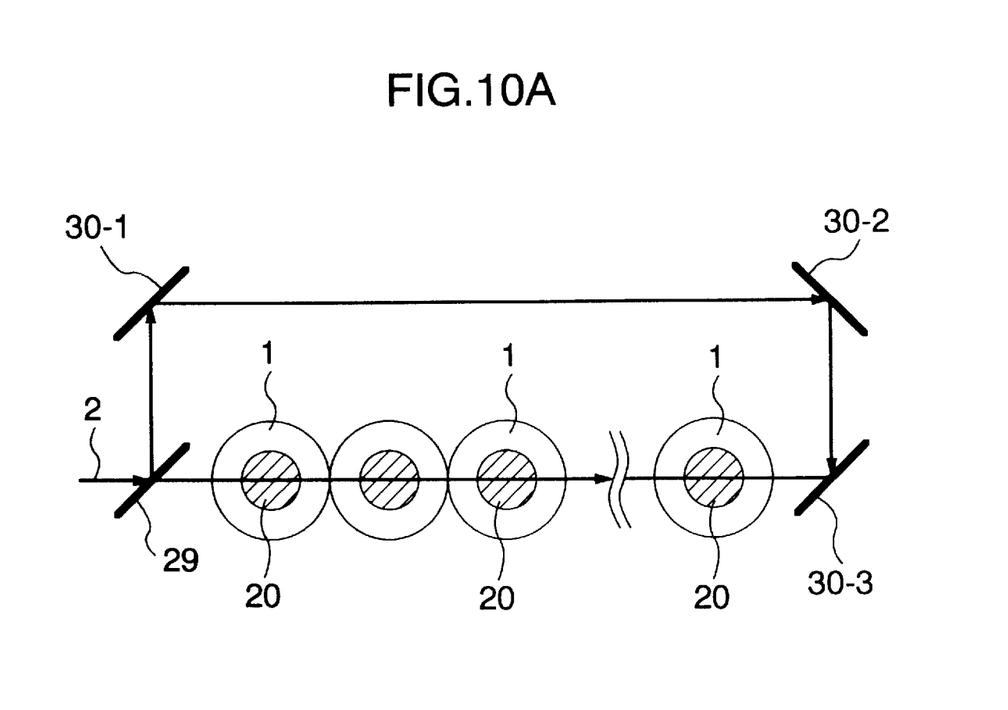
FIGS. 10A and 10B are diagrams illustrating the fifth example of the present invention and a construction in which laser beams are irradiated from two directions so that they can pass through respective capillary axes, FIG. 10A illustrating a construction in which laser beams are split by a translucent mirror and irradiated from two directions so that they can pass through respective capillary axes, and FIG. 10B illustrating another construction in which two laser beams are irradiated from two opposed directions to plurality of capillaries.
Figure 10B:
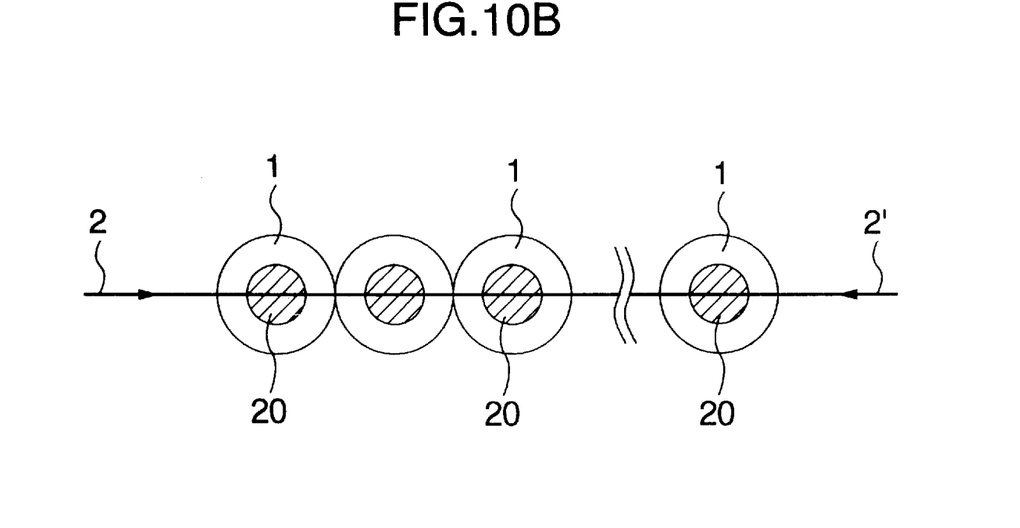

In the (First example) to (Fourth example) described above, constructions have been described in which a laser beam is irradiated from a direction through respective capillaries axes parallel with a plane made by the capillaries arranged in a plane shape, but they may also be constructions in which laser beams are irradiated from two directions through respective capillaries axes in the (First example) to (Fourth example) as shown in FIGS. 10A and 10B. The construction of FIG. 10A is one in which the laser beam 2 (laser with a single wavelength, or it may be a laser formed by mixing laser beams with multiple wavelengths coaxial to make coaxial) divided by a half mirror 29 and reflected by mirrors 30-1, 30-2 and 30-3 is irradiated from two directions through respective capillary axes. The construction of FIG. 10B is one in which two laser beams 2 and 2' are irradiated from two counterposed directions to a plurality of capillaries, where the laser beams 2 and 2' may be lasers respectively with a single wavelength or lasers formed by mixing laser beams with multiple wavelengths coaxial to make coaxial.

In the constructions of FIGS. 10A and 10B, the reduction of the intensity of the laser irradiated to respective capillaries in the (First example) to (Fourth example) is improved, irradiating a laser with higher intensity to respective capillaries. This results in allowance of a capillary array electrophoresis using more capillaries. In addition, a laser source of high output is preferably used in the construction of FIG. 10A because the laser irradiation intensity is reduced since the laser beam is divided. Furthermore, on applying the construction of FIG. 10B to the (First example) to (Fourth example), the wavelength of the single or multiple lasers contained in the laser beam 2 shall be either the same as or different from the wavelength of the single or multiple lasers contained in the laser beam 2'.

In FIGS. 10A and 10B, the examples have been described by using the construction of the capillary array shown in FIG. 1 for instance, but the examples, not limited to the capillary array shown in FIG. 1, can be applied to the construction of a capillary array comprising a focusing lens as shown in FIGS. 3, 4, 6, 7A, 7B, 9A and 9B, and further applied to a case as shown in FIG. 8, in which samples are detected in a sheath-flow.

As described above, the present invention enables a capillary array electrophoresis system which irradiates a plurality of capillaries substantially at the same time in a batch and detects fluorescence from samples, without mechanically scanning the plurality of capillaries or optically scanning a light beam.

We claim:

1. A capillary electrophoresis system comprising:
   a plurality of capillaries filled with a migration medium in which samples labeled with fluorophores migrate;
   a light source providing an excitation light exciting said fluorophores;
   a photo detector detecting a fluorescence emitted from said fluorophores; and
   light focusing means placed between said plurality of capillaries to which said excitation light is irradiated,
   wherein the parts of said plurality of capillaries to which said excitation light is irradiated are parallel and define a plane in which said light focusing means are arranged, and said excitation light is irradiated through said plurality of capillaries and said light focusing means.

2. A capillary electrophoresis system according to claim 1, wherein said capillaries and said light focusing means are arranged alternatively in a position irradiated by said excitation light.

3. A capillary electrophoresis system according to claim 1 wherein said light focusing means consist of cylindrical rod lenses being, the axes of said cylindrical rod lenses placed substantially in parallel with said capillaries.

4. A capillary electrophoresis system according to claim 1, wherein said light focusing means are capillaries filled with a liquid or a solid.

5. A capillary electrophoresis system according to claim 1, wherein said light focusing means are spherical or globular lenses arranged on the irradiation axis of said excitation light.

6. A capillary electrophoresis system according to claim 1, wherein the parts of said plurality of capillaries to which said excitation light is irradiated and said light focusing means are placed in a liquid.

7. A capillary electrophoresis system according to claim 6, wherein said liquid is water.

8. A capillary electrophoresis system according to claim 1, wherein reflection reducing coatings are formed on the external surfaces of at least the parts where said excitation light is irradiated in said plurality of capillaries and said light focusing means.

9. A capillary electrophoresis system comprising:
a plurality of quartz capillaries filled with a migration medium with 1.40 or a higher refractive index in which samples labeled with fluorophores migrate;
a light source providing an excitation light exciting said fluorophores;
a photo detector detecting a fluorescence emitted from said fluorophores; and
cylindrical rod lenses placed between said plurality of capillaries to which said excitation light is irradiated;
wherein the parts of said plurality of capillaries to which said excitation light is irradiated are parallel and define a plane in which said cylindrical rod lenses are arranged, and the parts of said plurality of capillaries are placed in water, and said excitation light is irradiated through said plurality of capillaries and said cylindrical rod lenses, and the axes of said cylindrical rod lenses are placed substantially in parallel with said capillaries.

10. A capillary electrophoresis system comprising:
a plurality of quartz capillaries filled with a migration medium with a 1.40 or a higher refractive index in which samples labeled with fluorophores migrate;
a light source providing an excitation light exciting said fluorophores;
a photo detector detecting a fluorescence emitted from said fluorophores; and
spherical or globular lenses placed between said plurality of capillaries to which said excitation light is irradiated;
wherein the parts of said plurality of capillaries to which said excitation light is irradiated are parallel and define a plane in which said spherical or globular lenses are arranged, and the parts of said plurality of capillaries are placed in water, and said excitation light is irradiated through said plurality of capillaries and said spherical or globular lenses, and said spherical or globular lenses are arranged on the irradiation axis of said excitation light.

11. A capillary electrophoresis system comprising:
a plurality of quartz capillaries filled with a migration medium with 1.40 or a higher refractive index in which samples labeled with fluorophores migrate;
a light source providing an excitation light exciting said fluorophores;
a photo detector detecting a fluorescence emitted from said fluorophores; and
light focusing means placed between said plurality of capillaries to which said excitation light is irradiated,
wherein the parts of said plurality of capillaries to which said excitation light is irradiated are parallel and define a plane in which said light focusing means are arranged, and the parts of said plurality of capillaries are placed in water, and said excitation light is irradiated through said plurality of capillaries and said light focusing means.

12. A capillary electrophoresis system according to claim 11, wherein said light focusing means consist of cylindrical rod lenses, the axes of said cylindrical rod lenses being placed substantially in parallel with said capillaries.

13. A capillary electrophoresis system according to claim 11, wherein said light focusing means are spherical or globular lenses arranged on the irradiation axis of said excitation light.

14. A capillary electrophoresis system comprising:
a plurality of quartz capillaries filled with a migration medium with 1.40 or a higher refractive index in which samples labeled with fluorophores migrate;
a light source providing an excitation light exciting said fluorophores;
a photo detector detecting a fluorescence emitted from said fluorophores; and
light focusing means placed every 6 or less of said capillaries,
wherein the parts of said plurality of capillaries to which said excitation light is irradiated are parallel and define a plane in which said light focusing means are arranged, and the parts of said plurality of capillaries are placed in water, and said excitation light is irradiated through said plurality of capillaries and said light focusing means.

15. A capillary electrophoresis system according to claim 14, wherein said light focusing means consist of cylindrical rod lenses, the axes of said cylindrical rod lenses are placed substantially parallel with said capillaries.

16. A capillary electrophoresis system according to claim 14 wherein said light focusing means are spherical or globular lenses arranged on the irradiation axis of said excitation light.

17. A capillary electrophoresis system comprising:
a plurality of quartz capillaries filled with a migration medium with 1.38 or a higher refractive index in which samples labeled with fluorophores migrate;
a light source providing an excitation light exciting said fluorophores;
a photo detector detecting a fluorescence emitted from said fluorophores; and
light focusing means placed after every 5 or less of said capillaries,
wherein the parts of said plurality of capillaries to which said excitation light is irradiated are parallel and define a plane in which said light focusing means are arranged, and the parts of said plurality of capillaries are placed in water, and said excitation light is irradiated through said plurality of capillaries and said light focusing means.

18. A capillary electrophoresis system according to claim 17, wherein said light focusing means consist of cylindrical rod lenses, the axes of said cylindrical rod lenses being placed substantially in parallel with said capillaries.

19. A capillary electrophoresis system according to claim 17, wherein said light focusing means are spherical or globular lenses arranged on the irradiation axis of said excitation light.

20. A capillary electrophoresis system comprising:
a plurality of quartz capillaries filled with a migration medium with a refractive index within a range from 1.36 to 1.41 in which samples labeled with fluorophores migrate;
a light source providing an excitation light exciting said fluorophores;

a photo detector detecting a fluorescence emitted from said fluorophores; and light focusing means placed alternatively with said capillaries, wherein the parts of said plurality of capillaries to which said excitation light is irradiated are parallel and define a plane in which said light focusing means are arranged, and the parts of said plurality of capillaries are placed in water, and said excitation light is irradiated through said plurality of capillaries and said light focusing means.

21. A capillary electrophoresis system according to claim 20, wherein said light focusing means consist of cylindrical rod lenses being, the axes of said cylindrical rod lenses placed substantially in parallel with said capillaries.

22. A capillary electrophoresis system according to claim 20, wherein said light focusing means are spherical or globular lenses arranged on the irradiation axis of said excitation light.

23. A capillary electrophoresis system comprising:

a plurality of capillary arrays each having a plurality of capillaries filled with a migration medium in which samples labeled with fluorophores migrate, and each having light focusing means arranged between the plurality of capillaries at the ends of the plurality of capillaries;

a light source radiating an excitation light which excites said fluorophores at ends of the respective plurality of capillary arrays; and a light detector which detects the fluorescence emitted from said fluorophores, wherein in each of said plurality of capillary arrays, the parts of the plurality of capillaries to which by the exciting light is irradiated are parallel and define a planar portion in which said light focusing means are arranged, and the excitation light is irradiated through the parts of the plurality of capillaries and the light focusing means, said planar portions of said capillary arrays overlapping one another with their edges staggered in the length direction of the capillary arrays.

24. A capillary electrophoresis system according to claim 23, wherein said light focusing means consist of cylindrical rod lenses being, the axes of said cylindrical rod lenses placed substantially in parallel with said capillaries.

25. A capillary electrophoresis system according to claim 23, wherein said light focusing means are spherical or globular lenses arranged on the irradiation axis of said excitation light.

* * * * *